(12) United States Patent
Morris et al.

(10) Patent No.: US 6,190,170 B1
(45) Date of Patent: Feb. 20, 2001

(54) AUTOMATED TOOTH SHADE ANALYSIS AND MATCHING SYSTEM

(75) Inventors: Alan C. Morris, Salt Lake City, UT (US); Craig A. Mabrito, Bellaire, TX (US); Matthew R. Roberts, Idaho Falls, ID (US)

(73) Assignee: Dentech, LLC, Salt Lake City, UT (US)

( * ) Notice: Under 35 U.S.C. 154(b), the term of this patent shall be extended for 0 days.

(21) Appl. No.: 09/234,585

(22) Filed: Jan. 21, 1999

Related U.S. Application Data (60) Provisional application No. 60/084,354, filed on May 5, 1998.

(51) Int. Cl.[7] .................................................... A61C 5/00
(52) U.S. Cl. ......................... 433/215; 433/26; 433/203.1
(58) Field of Search ................................. 433/26, 203.1, 433/215

(56) References Cited

U.S. PATENT DOCUMENTS

| | | |
|---|---|---|
| 3,986,777 | 10/1976 | Roll . |
| 4,110,826 | 8/1978 | Mollgaard et al. . |
| 4,654,794 | 3/1987 | O'Brien . |
| 4,813,000 | 3/1989 | Wyman et al. . |
| 5,055,040 | 10/1991 | Clar . |
| 5,383,020 | 1/1995 | Vieillefosse . |
| 5,529,492 | 6/1996 | Yarovesky et al. . |
| 5,690,486 | 11/1997 | Zigelbaum . |
| 5,745,229 | 4/1998 | Jung et al. . |
| 5,759,030 | 6/1998 | Jung et al. . |
| 5,766,006 | 6/1998 | Murljacic . |
| 5,961,324 | 10/1999 | Lechmann . |

*Primary Examiner*—Nicholas D. Lucchesi
(74) *Attorney, Agent, or Firm*—Trask Britt (57) ABSTRACT

A patient's dental prosthesis (e.g., a prosthesis tooth, crown, veneer, or bridge) is made by acquiring an image of the patient's teeth that contains black and white normalization references. These references are black and white porcelain, for example, that allow software of the invention to determine absolute black and absolute white within the image. The image is then normalized in accordance with the normalization references, which corrects the image for variations in lighting conditions and image source. The normalized image is then standardized by matching the pixels of the normalized image to selected shade standards. The dental prosthesis can then be manufactured by a lab technician by referring to the standardized image. The tooth shade analysis and matching system is also applicable to direct restorations of natural teeth, such as repair of chipped or broken teeth.

19 Claims, 13 Drawing Sheets

AUTOMATED TOOTH SHADE ANALYSIS AND MATCHING SYSTEM

This application claims the benefit of U.S. Provisional Application No. 60/084,354, filed May 5, 1998.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Technical Field

This invention relates in general to systems for color matching and, more specifically, to systems for analyzing and matching tooth shades. Such systems are of particular use in manufacturing dental prosthetics (e.g., crowns, bridges, veneers, and prosthetic teeth) to repair, replace or alter natural teeth, in various dental tooth whitening procedures and to enable communication between patient, dentist and lab technician concerning such procedures.

2. State of the Art

Dentists often repair or replace a diseased, damaged, or unsightly natural tooth of a patient with a crown, bridge, veneer, or prosthetic tooth. One obvious goal in performing such a repair or replacement is to provide the patient with a natural-looking smile despite the presence of the prosthesis. Attempts to reach this goal generally involve matching the color of the prosthesis to the color of the natural tooth being repaired or replaced, and to the colors of the natural teeth that are adjacent where the prosthesis will be placed.

Similarly, dentists often perform various tooth whitening procedures on a patient's natural teeth to reverse the effects of aging, coffee drinking, smoking, and similar activities on the patient's dental appearance. The goal in such procedures is also to provide the patient with a natural-looking smile, and attempts to reach this goal also generally involve color matching.

Figure 1:
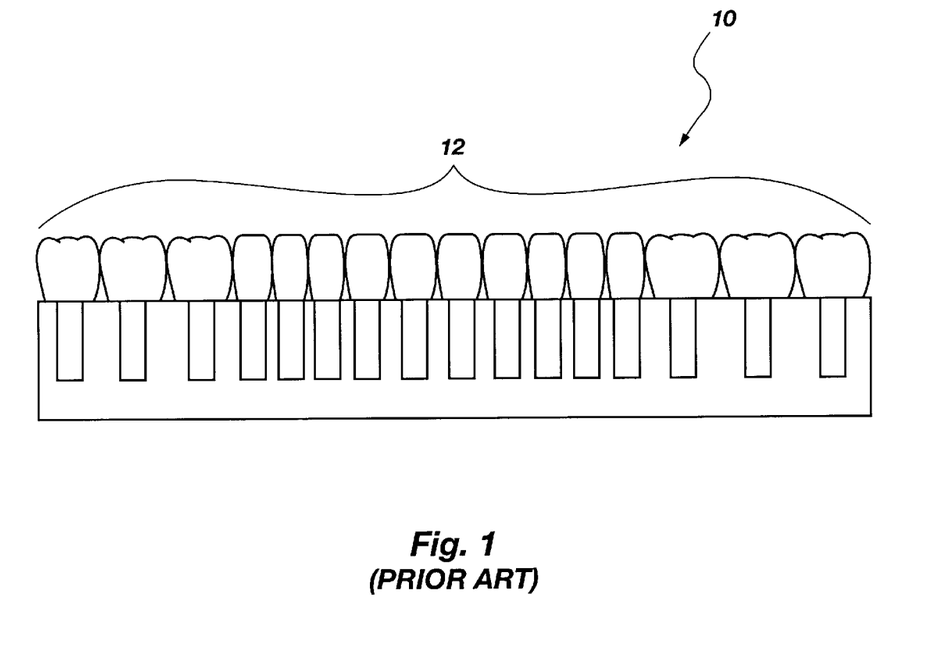
FIG. 1 is a side view of a conventional shade guide.

To this end, manufacturers of the various colored porcelains, resins, compomers ceramers or other direct restorative materials conventionally used in making dental prosthetics, or in repairing discolored, chipped, broken or malformed teeth, typically provide color matching shade guides to dentists which illustrate the various colored porcelains available. As shown in FIG. 1, one such shade guide 10 includes a variety of shade tabs 12, each made of a different colored porcelain available from a manufacturer. A dentist determines the color of a patient's natural teeth by detaching individual shade tabs 12 from the shade guide 10 and holding the shade tabs 12 next to the patient's natural teeth for comparison. Once a color match is found, the dentist orders a dental prosthesis from a dental laboratory in the matching colored porcelain or other material, or, if the patient's teeth are being whitened, the dentist uses the color match as a base against which to compare the eventual results of the whitening process.

This somewhat rudimentary method often provides less than desirable results because of the inaccuracy inherent in the dentist "eyeballing" the color match. Poor lighting, poor vision, eye fatigue, conflicting ambient colors or even lack of patient cooperation in the process, among other things, can cause the dentist to miss the best match. More importantly, the best match is often a combination of two or more colored porcelains, sometimes from different manufacturers, which is difficult to discern by the human eye.

Accordingly, a variety of mechanical and electronic devices have been devised to aid in matching tooth shades. Some of these devices are described in U.S. Pat. Nos. 5,766,006 to Murljacic, 5,759,030 to Jung et al., 5,690,486 to Zigelbaum, 5,529,492 to Yarovesky et al., 5,383,020 to Vieillefosse, 5,055,040 to Clar, 4,654,794 to O'Brien, and 4,110,826 to Möllgaard. Unfortunately, none of these devices has been very successful in advancing the tooth shade matching process much beyond the "eyeballing" procedure described above.

Therefore, there is a need in the art for an improved tooth shade matching system.

SUMMARY OF THE INVENTION

In accordance with the present invention, a computer-aided system provides apparatus and methods for capturing an image of a patient's teeth and analyzing such image with respect to the inherent tooth coloration and shading characteristics of the patient's teeth for the purposes of reproducing such inherent coloration and shading in restorative procedures and prosthetics.

In one embodiment of the invention, for example, a dental prosthesis for a patient is made by acquiring at least one image of the patient's teeth which contains normalization references. The image is then normalized in accordance with the normalization references. Next, the normalized image is standardized by matching the normalized image to selected shade standards, and the dental prosthesis is then made in accordance with the standardized image. The prosthesis may then be compared with the normalized image to assure a satisfactory product. The analysis and matching system of the present invention may be used not only in producing replacement prosthetics, such as dentures, bridges or caps, but is used in the restoration of broken, chipped or otherwise damaged or malformed teeth.

In another embodiment of this invention, a patient's teeth are whitened by acquiring at least one pre-whitening image of the patient's teeth, the image containing normalization references. The pre-whitening image is normalized in accordance with the normalization references contained therein, and the normalized pre-whitening image is then standardized by matching the normalized image to selected shade standards. The patient's teeth are then whitened. After whitening the patient's teeth, at least one post-whitening image of the patient's teeth containing normalization references is acquired, the post-whitening image is normalized in accordance with the normalization references contained therein, and the normalized post-whitening image is standardized by matching the normalized image to selected shade standards. Then, the standardized pre-whitening image and the standardized post-whitening image are compared.

In still another embodiment, image analysis is performed on a patient's teeth by acquiring at least one image of the patient's teeth containing normalization references. The image is then normalized in accordance with the normalization references contained therein, and the normalized image is standardized by matching the normalized image to selected shade standards. Communication between doctor, patient and lab technician is facilitated through the invention to provide each with the ability to select desired shades and/or colors of the eventual prosthesis, such as in cases of dental restoration, where a full or partial set of dentures is being produced.

In a further embodiment of this invention, a computer-readable storage medium stores a program for causing a computer to operate in accordance with the method for performing image analysis on a patient's teeth described immediately above.

In yet another embodiment, an apparatus for performing image analysis on a patient's teeth includes an input device for acquiring at least one image of the patient's teeth, the image containing normalization standards. Another device coupled to the input device normalizes the image in accordance with the normalization references contained therein and matches the normalized image to selected shade standards to standardize the normalized image.

In an additional embodiment of this invention, an electronic system incorporates the apparatus described immediately above.

DETAILED DESCRIPTION OF THE ILLUSTRATED EMBODIMENTS

Figure 2A:
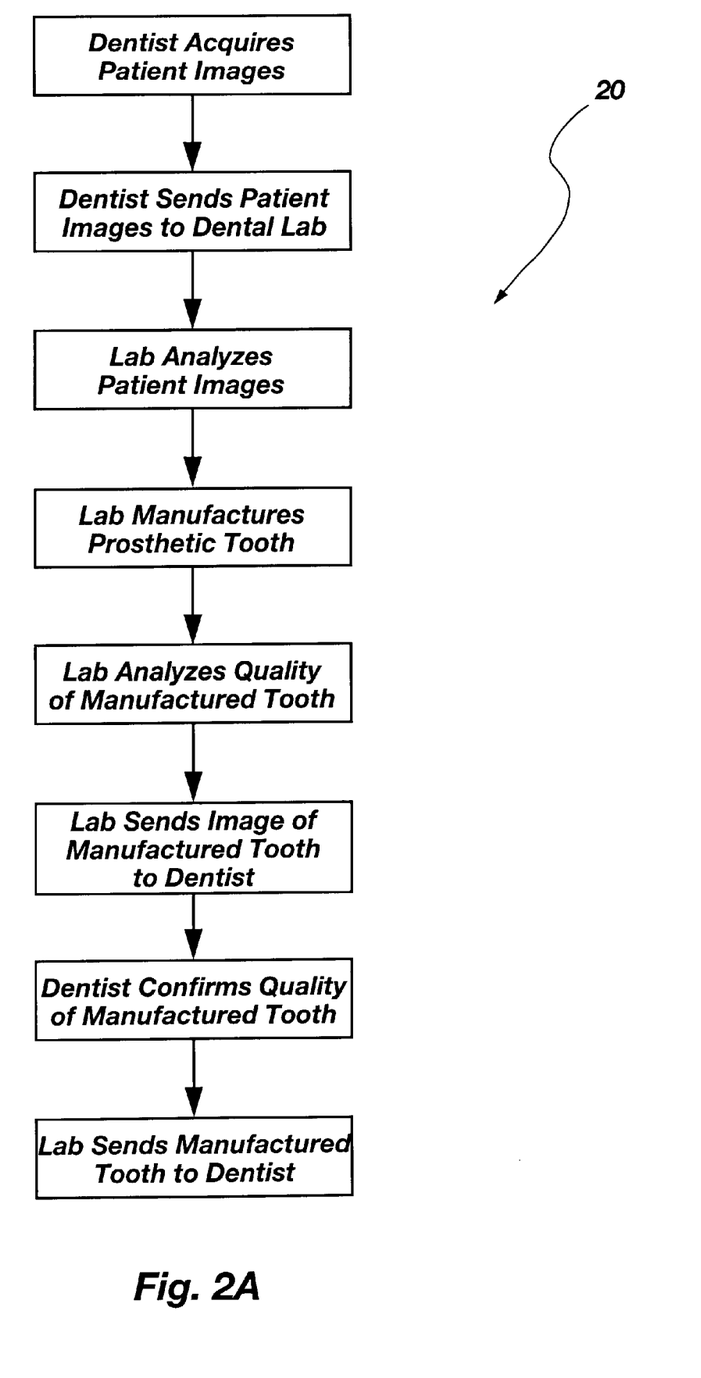
FIG. 2A is a flow diagram illustrating a prosthetic tooth manufacturing method of this invention.

As shown in FIG. 2A, a method 20 for manufacturing a prosthetic tooth in accordance with this invention begins with a dentist acquiring digital images of a patient's natural teeth. It should be noted that although this invention will be described with respect to the manufacturing of a prosthetic tooth or teeth, those having skill in the technical field of this invention will understand that the invention is applicable to manufacturing a wide variety of other dental prosthetics including, for example, crowns, bridges, removable dentures and veneers. Further, the invention described herein may be used for restoring a patient's natural teeth when, for example, a tooth becomes broken, chipped or modified from its original condition, thereby requiring some form of restoration, such as bonding or filling. It will also be understood that while a dentist will typically acquire the patient images, others may do so instead including, for example, a dental hygienist, assistant, or technician. Further, it will be understood that in some circumstances the "natural" teeth in the acquired images may actually include previously installed dental prosthetics.

Figure 2B:
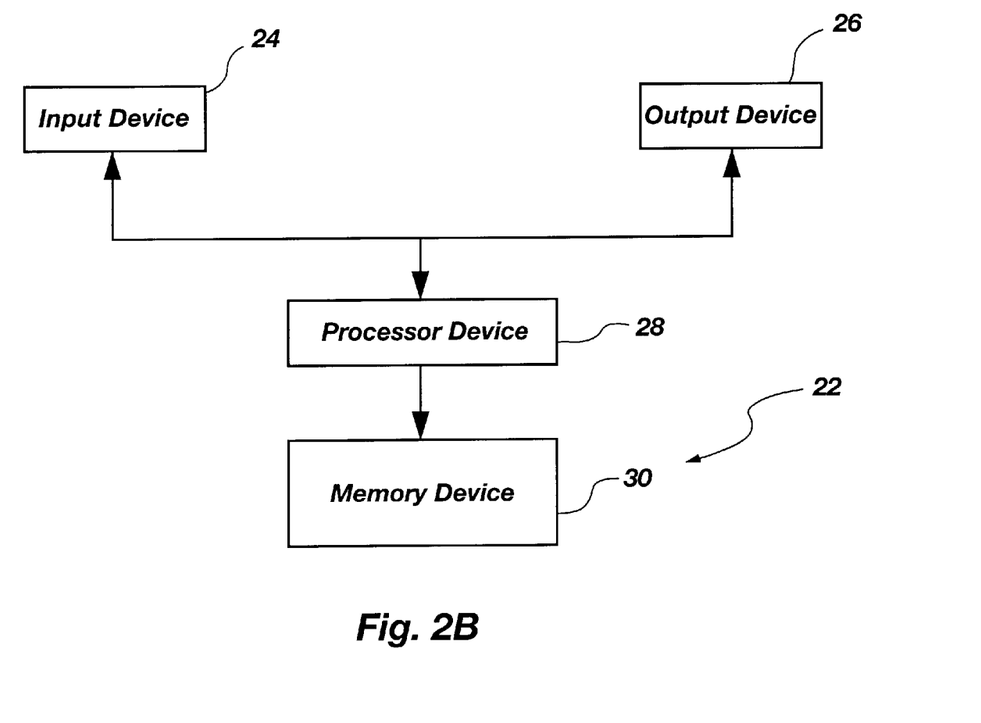
FIG. 2B is a block diagram illustrating an electronic system implementing the prosthetic tooth manufacturing method of FIG. 2A.

As shown in FIG. 2B, the method 20 (FIG. 2A) is implemented, in part, in software executing in an electronic system 22 comprising an input device 24, an output device 26, a processor device 28, and a memory device 30. The software may preferably be a Windows 95®- or Windows 98-compatible, 32-bit stand-alone application, but may instead be compatible with any other operating system or environment including, for example, UNIX, LINUX, the Apple OS, Windows® 3.x, and DOS. Also, the software may include, or be compliant with, ActiveX controls or Java Applets. The electronic system 22 is preferably an IBM-PC-compatible computer system, but may instead comprise any other computer or electronic system.

The dentist acquires the patient teeth images using the input device 24, which may be any suitable device for acquiring digital images including, for example: a standard or intra-oral analog color Charge Coupled Device (CCD) video camera providing a video feed to a TWAIN-compliant frame capture PC-card; a digital camera providing digital images directly to a 32-bit TWAIN driver through a SCSI port; and a color image scanner scanning photographic slides, pictures, and the like, and providing the resulting digital images directly to a 32-bit TWAIN driver through a SCSI port. Of course, the patient images may have previously been acquired and stored on a storage medium, such as a Jazz® or Zip® disc, in which case the dentist may "reacquire" them by transferring them from the storage medium to the electronic system 22.

In order to reduce shade variation in the patient images due to the camera angle at which the images are taken, it is preferable, but not necessary, that the dentist use standardized camera angles. For example, the dentist may take standard left, right, and straight-on pictures level with the patient's mouth. Of course, other standardized angles are also possible or helpful, such as inferior and superior angles.

Also, in order to reduce variations due to camera type, lighting conditions, etc., the dentist inserts black and white reference tabs into the images to provide references with respect to which the images may be normalized, as will be described in more detail below with respect to FIGS. 5A, 5B, and 5C. These black and white reference tabs are manufactured using homogeneous, non-reflective porcelains and are intended to define the respective minimum and maximum Red, Green, and Blue (RGB) values for each image.

Referring once again to FIG. 2A, after acquiring the patient images, the dentist sends the images to a dental laboratory for analysis by a lab technician. Of course, it should be understood that while this invention will be described in the context of a dentist taking the pictures and installing the prosthetic tooth and a lab technician performing the image analysis and manufacturing the prosthetic tooth, other arrangements are possible. For example, the dentist might perform the image analysis and send the analyzed images to the dental technician, or the patient's images may be taken at the dental laboratory by the lab technician. Also, although the description herein implies a degree of physical distance between the dentist's office and the dental laboratory, the dentist and the laboratory may, in fact, reside in close physical proximity, including within the same offices. Thus, the dentist and the lab technician may use the same computer system if they are located in the same offices, thereby eliminating the need for the dentist to "send" the images to the lab technician.

The dentist may send the patient images to a dental laboratory using a wide variety of means including, for example, an e-mail, an Internet download, a modem-to-modem download, and delivery of a storage medium, such as a Jazz® or Zip® disc, on which the images are stored.

Upon receiving the patient images, the lab technician analyzes the images using another electronic system 22 (FIG. 2B) adapted using software for his or her use in implementing another part of the method 20. As described herein, the dentist and the lab technician have nearly identical software executing on their respective electronic systems 22 (FIG. 2B). However, it will be understood that certain functions desirable in the lab technician's software (e.g., image analysis) may not be necessary to the dentist's software (and therefore may not be present therein), and vice-versa.

Figure 3:
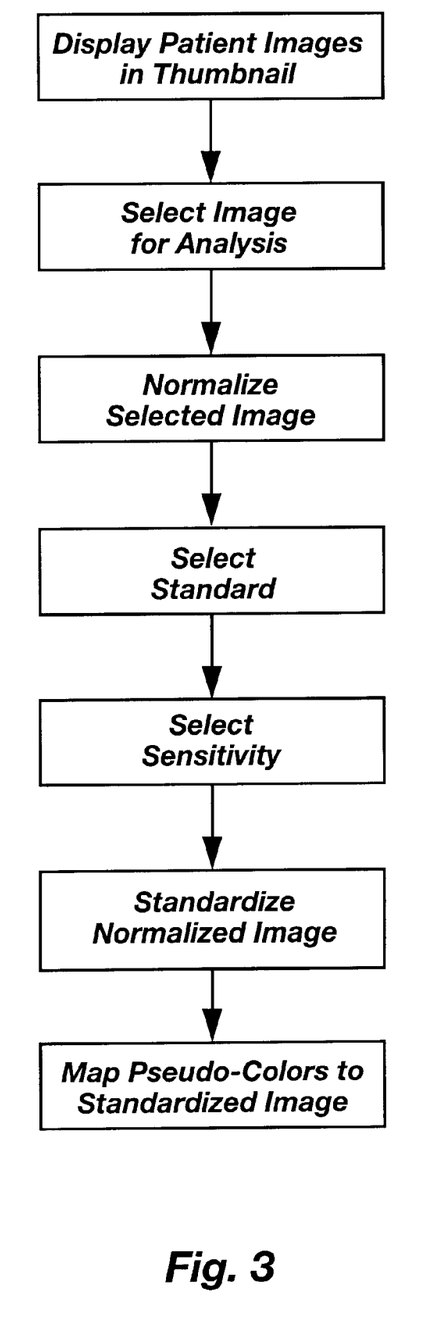
FIG. 3 is a flow diagram illustrating in more detail a patient image analysis procedure of the prosthetic tooth manufacturing method of FIG. 2A.
Figure 4:
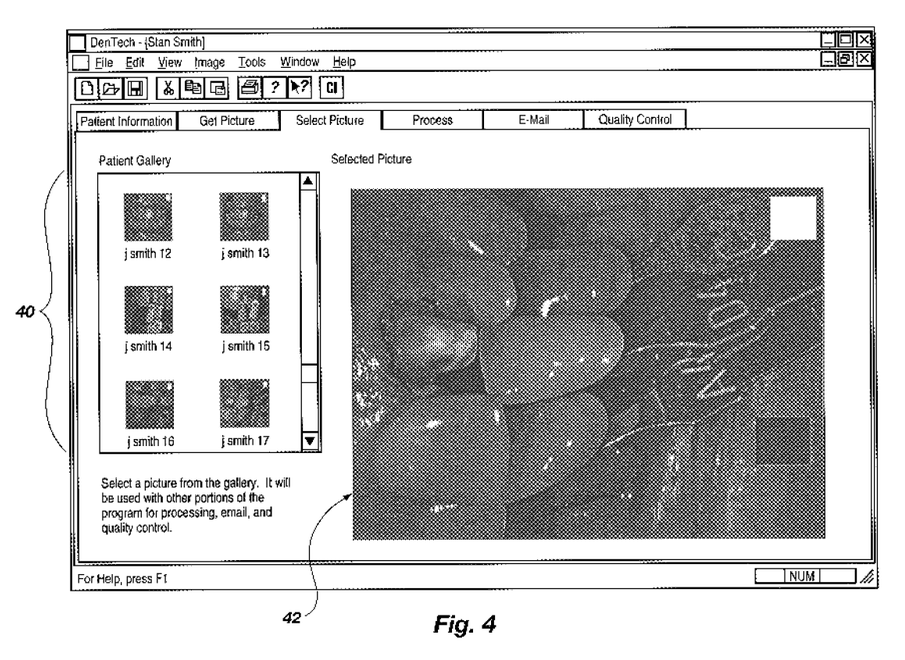
FIG. 4 is a screen capture illustrating a thumbnail gallery patient image display step and a patient image selection step of the patient image analysis procedure of FIG. 3.

As shown in FIGS. 3 and 4, the lab technician begins analysis of the images by displaying them in a thumbnail gallery 40. The lab technician then selects one of the images from the gallery 40 for analysis, and displays the selected image 42 in large format.

Figure 5A:
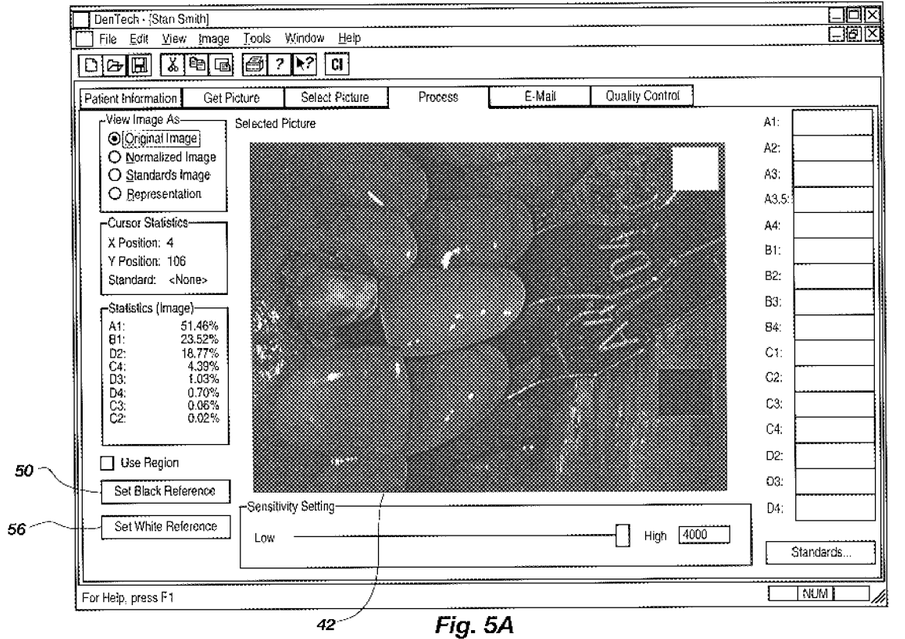
FIGS. 5A, 5B, and 5C are screen captures illustrating a patient image normalization step of the patient image analysis procedure of FIG. 3.
Figure 5B:
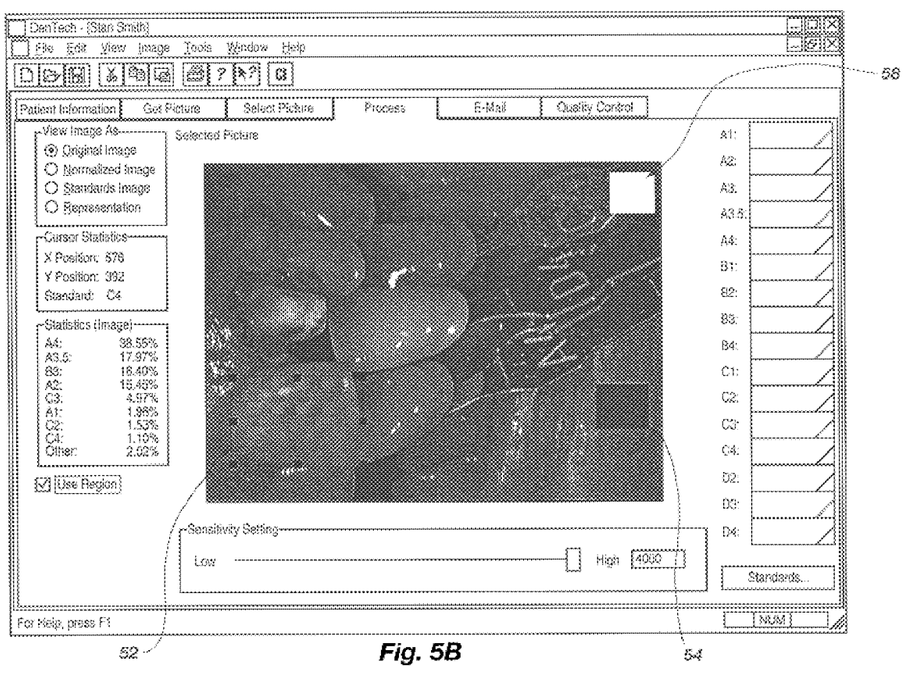

As shown in FIGS. 3, 5A and 5B, the lab technician continues the image analysis procedure by normalizing the selected image 42. The lab technician begins the normalization process by selecting a "Set Black Reference" button 50, and then adjusting and moving a selection area 52 so it identifies a black reference tab 54 previously inserted into the selected image 42 by the dentist. With the black reference tab 54 identified, the software executing on the lab technician's system 22 (FIG. 2B) then determines the Black Reference RGB value by determining the average red, green, and blue values among all the pixels in the selection area 52. A similar procedure involving a "Set White Reference" button 56, the selection area 52, and a white reference tab 58 allow for the determination of the average red, green, and blue values for a White Reference RGB value as well. The Black and White References may be generally referred to as "normalization references."

With the Black and White Reference RGB values determined, the software then calculates a normalized look-up table for the selected image 42. An example may help explain this aspect of the disclosure. Assume, for the moment, that each pixel of the selected image 42 is stored as an 8-bit index into a 256 color look-up table such as the following:

TABLE 1

| Index | Red | Green | Blue |
|---|---|---|---|
| 00000000 | 00000010 | 00000101 | 00000001 |
| 00000001 | 00000100 | 00000110 | 00000011 |
| 00000010 | 00000101 | 00000111 | 00000101 |
| . | . | . | . |
| . | . | . | . |
| . | . | . | . |
| 11111110 | 11110110 | 11111101 | 11111100 |
| 11111111 | 11111001 | 11111110 | 11111111 |

Under this circumstance, the software normalizes the look-up table by recalculating the red, green, and blue values for each index. The calculations are as follows:

New Red Value=(255÷Red Range)×(Index−Black Reference Red Value)+0.5                         (1)

New Green Value=(255÷Green Range)×(Index−Black Reference Green Value)+0.5        (2)

New Blue Value=(255÷Blue Range)×(Index−Black Reference Blue Value)+0.5           (3)

where

Red Range=White Reference Red Value−Black Reference Red Value                              (4)

Green Range=White Reference Green Value−Black Reference Green Value                    (5)

Blue Range=White Reference Blue Value−Black Reference Blue Value                        (6)

Of course, images that directly store the red, green, and blue values for each pixel (e.g., so-called "24-bit" images) and that, therefore, do not use a look-up table, may be normalized in much the same way, except that the normalization procedure is performed on the pixel values of the image itself, rather than on the values in a look-up table.

Figure 5C:
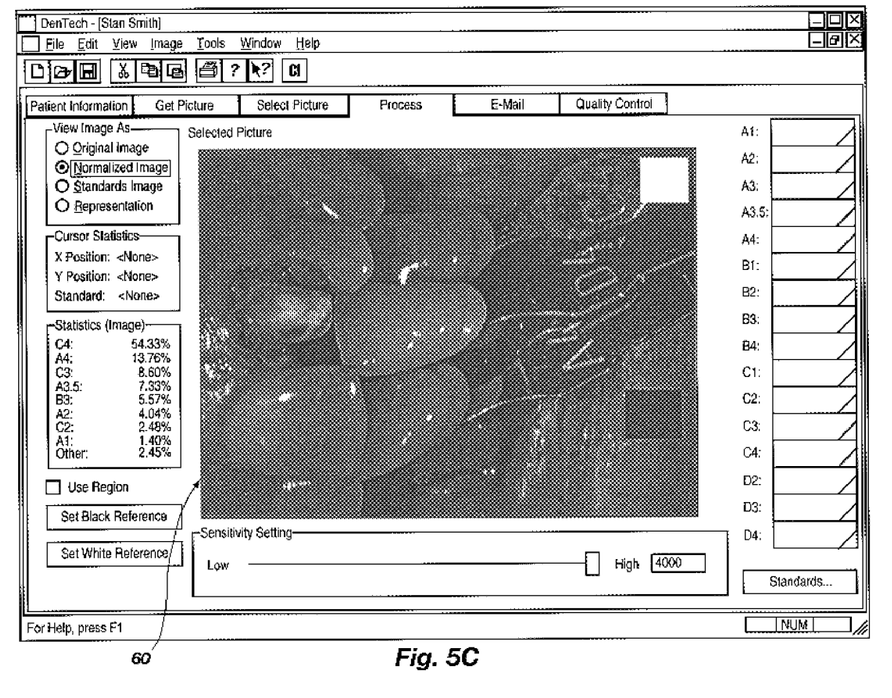

Continuing with the example described above, once the look-up table for the selected image 42 is normalized, the selected image 42 is redisplayed as a normalized image 60, as shown in FIG. 5C, using the normalized look-up table.

Figure 6:
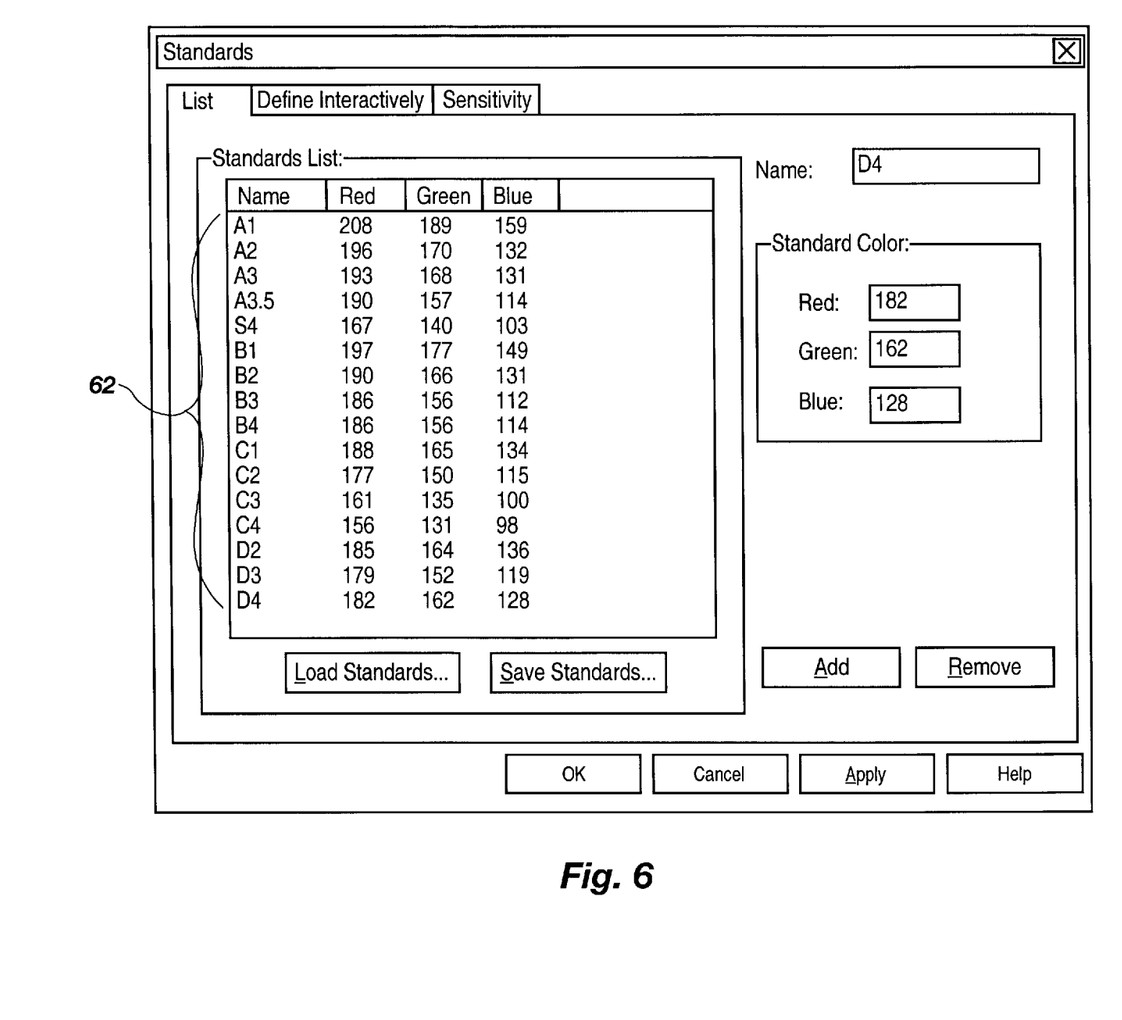
FIGS. 6 is a screen capture illustrating a standards selection step of the patient image analysis procedure of FIG. 3.

As shown in FIGS. 3 and 6, with the selected image 42 (FIG. 5A) normalized, the lab technician then selects the shade standards 62 to be used in manufacturing the prosthetic tooth. Although the shade standards can be generated from images of the conventional shade guides previously described, it is preferable that the shade standards be generated from flat, non-reflective, homogeneous porcelain samples. This is because the conventional shade guides are manufactured to look like a conventional tooth, and thus, are curved, semi-glossy, and non-homogeneous in the porcelain shade they represent. Thus, for example, a conventional shade standard "a-1" shade tab is made to look like a tooth, so it is curved, semi-glossy, and is only a true "a-1" porcelain in its center. The preferred flat, non-reflective, homogeneous porcelain samples are better adapted to provide accurate shade standards for digital image analysis.

Figure 7A:
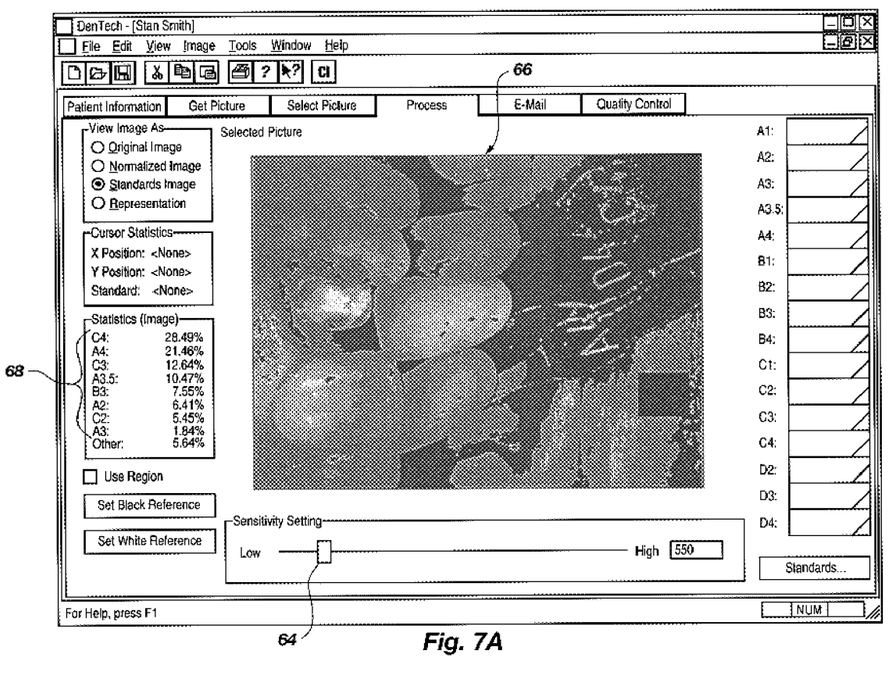
FIGS. 7A and 7B are screen captures illustrating a standardization sensitivity selection step and a standardization step of the patient image analysis procedure of FIG. 3.
Figure 7B:
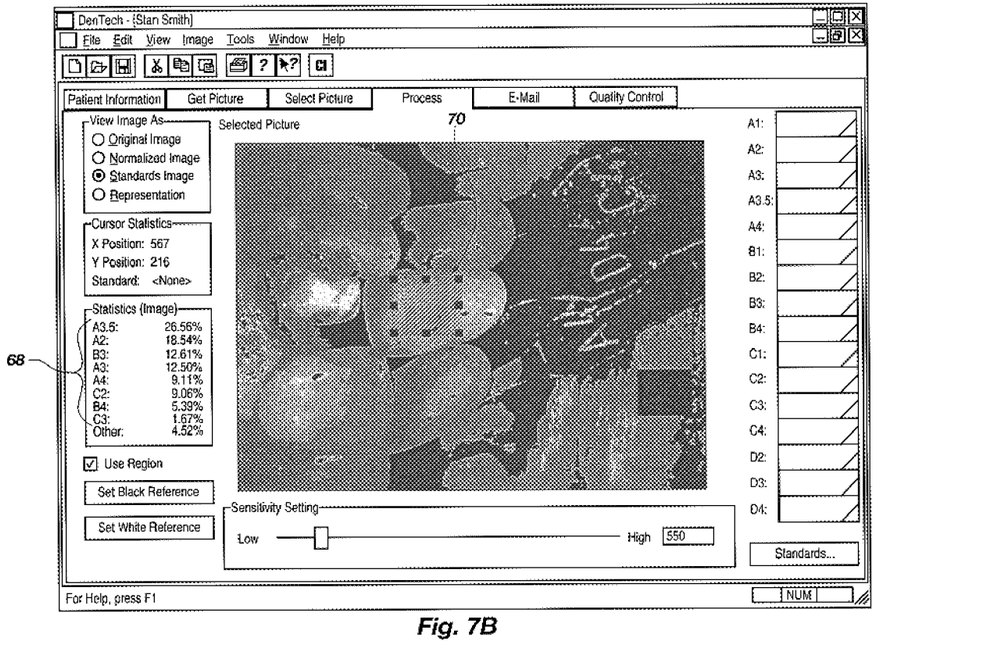

As shown in FIGS. 3, 7A, and 7B, with the shade standards selected, the lab technician then selects a standardization sensitivity level using a sensitivity selector 64, and the software then attempts to match each pixel in the normalized image 60 (FIG. 5C) to one of the selected standards. To accomplish this for each pixel, the software calculates a "distance" between the RGB values of the pixel and the RGB values of each of the selected standards, according to the following equation:

distance=$(R_{pixel}-R_{standard})^2+(G_{pixel}-G_{standard})^2+(B_{pixel}-B_{standard})^2$              (7)

The software then determines the standard having the minimum distance calculated. If this minimum distance does not exceed the sensitivity level (e.g., 4,000) set by the lab technician, the software determines that the standard with the minimum distance matches the pixel and assigns this standard color to the pixel. If, instead, the software determines that the minimum distance calculated exceeds the sensitivity level selected, then the software assigns the color black to the pixel. As shown in FIG. 7A, the software then displays a standardized image 66 with the colors assigned to each pixel.

It should be noted that the standardized image 66 is displayed alongside a statistical analysis 68 of the percentage of the image 66 occupied by the various standards. As shown in FIG. 7B, this statistical analysis 68 can also be confined to a selected region 70.

Figure 8:
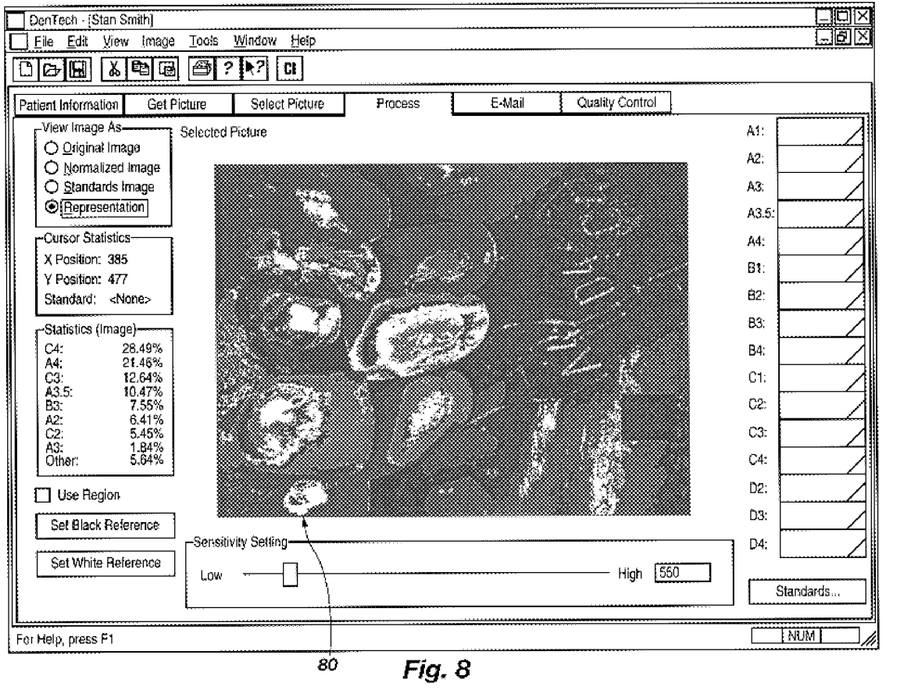
FIG. 8 is a screen capture illustrating a pseudo-color mapping step of the patient image analysis procedure of FIG. 3.

As shown in FIG. 8, pseudo-colors can be assigned to each standard to generate a pseudo-color image 80, in which the differences between various standards is easier to discern than in the standardized image 68 of FIG. 7B. Thus, for example, a standard shade "a-1", which may be a light tan color, may be assigned a pseudo-color of yellow, while a standard shade "a-2", which may be a slightly darker tan color, may be assigned a pseudo-color of grass green. As a result, while the distinctions between a-1 (light tan color) and a-2 (slightly darker tan color) may be difficult to discern from the standardized image 66, they readily stand out in the pseudo-color image 80 because of the contrasting yellow and grass green colors.

As shown in FIG. 2A, once the patient images have been analyzed, the lab technician manufactures the prosthetic tooth using the pseudo-color image 80 (FIG. 8) as a guide.

Figure 9:
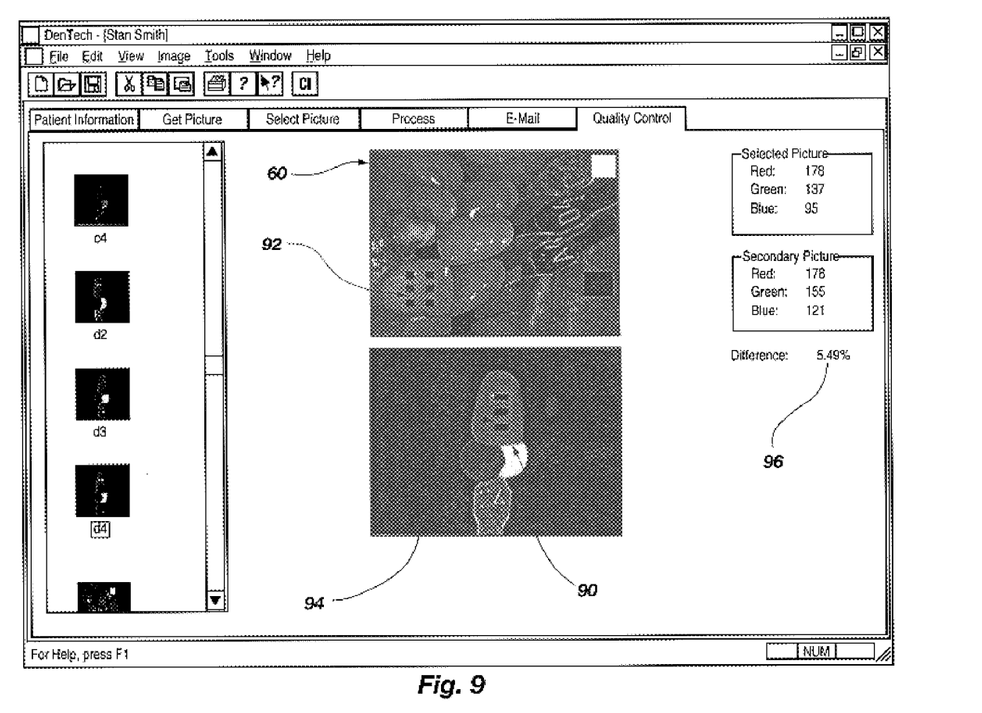
FIG. 9 is a screen capture illustrating a quality analysis step of the prosthetic tooth manufacturing method of FIG. 2A.

As shown in FIGS. 2A and 9, the lab technician then analyzes the quality of the prosthetic tooth 90 by comparing a normalized image of the prosthetic tooth 90 with the normalized image 60 of the patient's natural tooth using the software. Specifically, the technician selects the natural tooth and the prosthetic tooth using selection regions 92 and 94, and the software then calculates the average difference 96 in shades between the two regions 92 and 94. A dentist may specify that the prosthetic tooth must not exceed a certain maximum average difference (e.g., 10%), and the dental laboratory may charge different fees for prosthetic teeth guaranteed to fall below certain maximum average differences (e.g., $500 for 2%, $300 for 5%, $150 for 10%, etc.).

Once the lab technician has confirmed that the prosthetic tooth meets the specified quality standard, the technician can send an image of the prosthetic tooth to the dentist so the dentist can confirm the quality of the tooth using his own software in the same manner as described immediately above. The dentist can then contact the patient so that the dentist and patient can confer and agree as to the acceptability of the prosthesis. The dentist may confer in-person with the patient or may transmit the image to the patient by electronic mail for review and discussion. If changes are required, those can be conveyed to the lab technician for implementation into the image for final review before the actual prosthetic tooth is completed. Once the dentist authorizes delivery of the prosthetic tooth, the lab technician sends the tooth to the dentist, and the dentist installs the tooth in the patient.

It should be understood that while this invention has been described with respect to a process for manufacturing a prosthetic tooth or bridge or dentures, the system is equally applicable to restoration of teeth in the dentist's office when, for example, a patient's tooth is broken, chipped or otherwise modified from its original condition, and in such instances, the dentist may prepare the image and analyze it within his office to determine an accurate restoration of the tooth. The system of the invention is equally applicable to a process for teeth whitening. In such a process, the image analysis procedures described herein are used to determine the shade of a patient's teeth and then to compare the shade of the post-whitening teeth to the shade of the pre-whitening teeth.

It should also be understood that while this invention has been described with respect to colors described in the RGB format, the invention may alternatively incorporate any other applicable format for describing colors including, for example, the Hue, Saturation, and Luminance (HSL) or Hue, Value and Chroma format.

Figure 10:
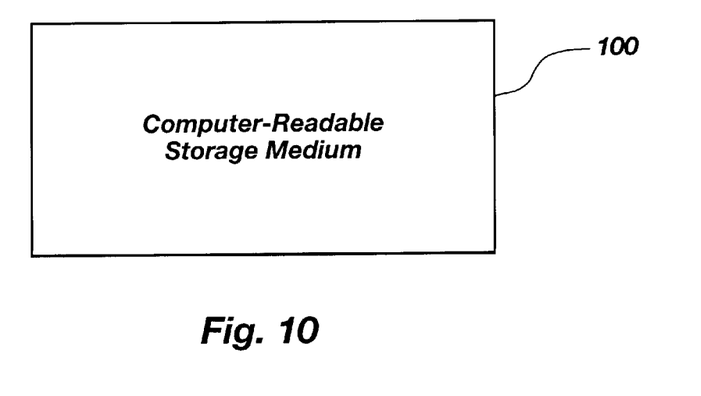
FIG. 10 is a diagram illustrating a computer-readable storage medium storing software implementing the prosthetic tooth manufacturing method of FIG. 2A.

As shown in FIG. 10, a computer-readable storage medium 100 stores the software previously described. The storage medium 100 may be, for example, a floppy disc, a Jaz® or Zip® disc, a hard drive, a CD-ROM, a DVD-ROM, a flash EEPROM card, a magnetic tape, or a ROM, PROM, EPROM, EEPROM, or flash EEPROM chip.

Although this invention has been described with reference to particular embodiments, the invention is not limited to these described embodiments. For example, while the various steps and procedures of the methods of this invention have been described as occurring in a particular order, the invention is not limited to the described order. Rather, the invention is limited only by the appended claims, which include within their scope all equivalent devices or methods that operate according to the principles of the invention as described.

What is claimed is:

1. A method of effecting a dental repair or replacement, the method comprising:
   acquiring at least one image of a patient's teeth containing normalization references;
   normalizing the at least one image in accordance with the normalization references contained therein;
   standardizing the normalized at least one image by matching the normalized image to selected shade standards; and
   producing a restorative modification of the patient's teeth in accordance with the standardized image.

2. The method of claim 1, wherein acquiring the at least one image containing normalization references comprises acquiring the at least one image containing black and white normalization references.

3. The method of claim 1, wherein acquiring the at least one image includes acquiring the at least one image using an input device selected from a group comprising a digital camera, an analog camera, a scanner, and a computer-readable storage medium.

4. The method of claim 1, wherein acquiring the at least one image includes acquiring the at least one image in digital form with pixels of the at least one image represented in a Red-Green-Blue (RGB) format.

5. The method of claim 1 wherein said restorative modification of the patient's teeth comprises manufacturing a dental prosthetic.

6. The method of claim 5, wherein acquiring the at least one image, normalizing the image, standardizing the at least one image, and making the dental prosthesis occur in sequential order.

7. The method of claim 1, further comprising sending the acquired at least one image to a dental laboratory using a delivery means selected from a group comprising electronic mail, an Internet download, a modem-to-modem download, and a computer-readable storage medium.

8. The method of claim 1, wherein acquiring the at least one image comprises acquiring the at least one image containing black and white normalization references, and wherein normalizing the at least one image includes normalizing a look-up table associated with the at least one image.

9. The method of claim 1, wherein acquiring the at least one image comprises acquiring the at least one image containing black and white normalization references, and wherein normalizing the at least one image comprises recalculating the Red, Green, and Blue values associated with each pixel of the at least one image to normalize each pixel with respect to the black and white normalization references.

10. The method of claim 1, wherein standardizing the normalized at least one image comprises:

selecting a standardization sensitivity level;

determining a color distance between the Red, Green, and Blue values associated with each pixel of the normalized at least one image and each of the selected shade standards;

determining a minimum color distance for each pixel; and for each pixel, when the minimum color distance for the pixel is less than the selected standardization sensitivity level, matching the selected shade standard associated with the minimum color distance to the pixel.

11. The method of claim 1, further comprising mapping pseudo-colors representative of each of the selected shade standards onto the standardized image to form a pseudo-color image.

12. The method of claim 1, wherein restorative modification of the patient's teeth comprises repairing broken, chipped or damaged teeth.

13. The method of claim 1, further comprising comparing the average Red, Green, and Blue values of an image of the dental prosthesis with the average Red, Green, and Blue values of the normalized at least one image.

14. A method of performing image analysis on a patient's teeth, the method comprising:

acquiring at least one image of the patient's teeth containing normalization references;

normalizing the at least one image in accordance with the normalization references contained therein; and standardizing the normalized at least one image by matching the normalized at least one image to selected shade standards.

15. An apparatus for performing image analysis on a patient's teeth, the apparatus comprising:

an input device for acquiring at least one image of the patient's teeth containing normalization standards; and a device coupled to the input device for normalizing the at least one image in accordance with the normalization references contained therein and matching the normalized at least one image to selected shade standards to standardize the normalized at least one image.

16. The apparatus of claim 15, wherein the input device is selected from a group comprising a digital camera, an analog camera, a scanner, and a computer-readable storage medium.

17. The apparatus of claim 15, wherein the normalizing and matching device comprises a processor device.

18. An electronic system comprising an input device, an output device, a memory device, and a processor device coupled to the input, output, and memory devices, one or more of the input, output, processor, and memory devices comprising an apparatus for performing image analysis on a patient's teeth, the apparatus comprising:

an input device for acquiring at least one image of the patient's teeth containing normalization standards; and a device coupled to the input device for normalizing the at least one image in accordance with the normalization references contained therein and matching the normalized at least one image to selected shade standards to standardize the normalized at least one image.

19. The electronic system of claim 18, wherein the electronic system comprises a computer system.

* * * * *

UNITED STATES PATENT AND TRADEMARK OFFICE
CERTIFICATE OF CORRECTION

PATENT NO. : 6,190,170 B1
APPLICATION NO. : 09/234585
DATED : February 20, 2001
INVENTOR(S) : Alan C. Morris, Craig A. Mabrito and Matthew R. Roberts It is certified that error appears in the above-identified patent and that said Letters Patent is hereby corrected as shown below:

On the title page:
In ITEM (56) References Cited,
  2$^{nd}$ column, after last entry,    insert
                         --OTHER DOCUMENTS
              International Search Report, dated July 16, 1999.--

Signed and Sealed this

Twenty-fifth Day of December, 2007

JON W. DUDAS
*Director of the United States Patent and Trademark Office*